United States Patent [19]

Kolts et al.

[11] Patent Number: 4,956,515

[45] Date of Patent: Sep. 11, 1990

[54] DEHYDROGENATION PROCESS AND CATALYST

[75] Inventors: John H. Kolts, Ochelata; Gary A. Delzer, Bartlesville, both of Okla.

[73] Assignee: Phillips Petroleum Company, Bartlesville, Okla.

[21] Appl. No.: 279,608

[22] Filed: Dec. 5, 1988

[51] Int. Cl.$^5$ .............................................. C07C 4/02
[52] U.S. Cl. .................................. 585/651; 585/653; 585/661
[58] Field of Search ............... 585/651, 562, 653, 661; 208/121

[56] References Cited

U.S. PATENT DOCUMENTS

| | | | |
|---|---|---|---|
| 2,942,960 | 6/1960 | Gerhold | 48/215 |
| 3,027,415 | 3/1962 | Steinhofer et al. | 585/653 X |
| 3,211,800 | 10/1965 | Bajars | 260/680 |
| 3,308,192 | 3/1967 | Bajars | 260/669 |
| 3,449,458 | 6/1969 | Tiedje et al. | 260/669 |
| 3,852,370 | 12/1974 | Hinkson et al. | 260/680 E |
| 4,044,067 | 8/1977 | Besozzi et al. | 260/680 E |
| 4,093,536 | 6/1978 | Heckelsberg | 585/653 X |
| 4,093,661 | 6/1978 | Trecker et al. | 260/595 |
| 4,159,970 | 7/1979 | Heckelsberg | 252/471 |
| 4,579,997 | 4/1986 | Kolts et al. | 585/653 |
| 4,613,722 | 9/1986 | Kolts et al. | 585/651 |
| 4,620,051 | 10/1986 | Kolts et al. | 585/663 |
| 4,620,052 | 10/1986 | Kolts et al. | 585/663 |
| 4,621,162 | 11/1986 | Delzer et al. | 585/651 |
| 4,621,163 | 11/1986 | Kolts | 585/653 |
| 4,705,769 | 11/1987 | Kolts et al. | 502/241 |

*Primary Examiner*—Patrick P. Garvin
*Assistant Examiner*—George R. Fourson
*Attorney, Agent, or Firm*—K. K. Brandes

[57] ABSTRACT

$C_3$ and/or $C_4$ hydrocarbons (in particular propane and butanes) are converted to less saturated hydrocarbons (in particular ethylene and propylene) in the presence of a catalyst consisting essentially of either (a) zinc oxide and manganese oxide or (b) zinc oxide, manganese oxide and calcium oxide. Compositions of matter (a) and (b), as defined above, are provided in accordance with this invention.

17 Claims, No Drawings

DEHYDROGENATION PROCESS AND CATALYST

BACKGROUND OF THE INVENTION

In one aspect, the present invention relates to a process for converting $C_3$ and $C_4$ hydrocarbons to less saturated hydrocarbons. In another aspect, this invention relates to novel compositions of matter which are useful as catalysts in a process for converting $C_3$ and $C_4$ hydrocarbons to less saturated hydrocarbons.

Processes for the catalytic conversion of $C_3$ and $C_4$ hydrocarbons to less saturated hydrocarbons are known, and have been described in U.S. Pat. Nos. 4,621,163; 4,621,162, 4,620,051 and 4,613,722. However, there is an ever present need to develop new catalysts which are more effective in these hydrocarbon conversion processes than known catalyst compositions.

SUMMARY OF THE INVENTION

It is an object of this invention to provide a process for converting $C_3$ and $C_4$ hydrocarbons to less saturated hydrocarbons (i.e., hydrocarbons containing less bound hydrogen than the feed hydrocarbons). It is another object to provide novel compositions of matter which are useful as catalyst compositions in a process for converting $C_3$ and $C_4$ hydrocarbons to less saturated hydrocarbons. Other objects and advantages will be apparent from the detailed description and the appended claims.

In accordance with this invention, a process for converting $C_3$ and/or $C_4$ hydrocarbons (in particular propane and butanes) to less saturated hydrocarbons (in particular ethylene and propylene) comprises contacting a feed comprising at least one hydrocarbon containing 3 or 4 carbon atoms per molecule (in particular propane or n-butane or isobutane or mixtures thereof) with a solid catalyst composition consisting essentially of a material selected from the group consisting of (a) zinc oxide and at least one manganese oxide, and (b) zinc oxide, at least one manganese oxide and calcium oxide, under such conditions as to convert at least a portion of the feed hydrocarbon(s) to at least one less saturated hydrocarbon. Preferably, the number of carbon atoms per molecule of the formed less saturated hydrocarbon(s) is less than that of the feed hydrocarbon(s).

In a preferred embodiment, zinc oxide is the support material and the major component in catalyst compositions (a) and (b), and manganese oxide is a minor component. In another preferred embodiment, the feed comprises (more preferably consists essentially of) n-butane. In still another preferred embodiment, steam is also present during the hydrocarbon conversion process.

Also in accordance with this invention, a composition of matter is provided which consists essentially of (i) zinc oxide as carrier (support material) and major component (i.e., being present at above 50 weight-% of the composition of matter) and (ii) at least one manganese oxide as minor component. This composition of matter consisting essentially of (i) and (ii) is effective as a catalyst composition for converting $C_3$ and $C_4$ hydrocarbons to less saturated hydrocarbons.

Further in accordance with this invention, a composition of matter is provided which consists essentially of (i) zinc oxide as carrier (support material) and major component, (ii) at least one manganese oxide as first minor component, and (iii) calcium oxide as second minor component. This composition of matter consisting essentially of (i), (ii) and (iii) is effective as catalyst composition for converting $C_3$ and $C_4$ hydrocarbons to less saturated hydrocarbons.

DETAILED DESCRIPTION OF THE INVENTION

The hydrocarbon feed, in accordance with the present invention, can include any hydrocarbon gas containing significant amounts of $C_3$ and/or $C_4$ hydrocarbons, particularly propane, n-butane (normal butane) and isobutane, with n-butane being presently preferred. Other normally gaseous components, or even normally liquid components which vaporize at operating conditions, can also be present if they are not detrimental to the process. Suitable feedstocks for the process of the present invention can be obtained from any source, including natural gas, refinery off-gases and the like, as has been described in U.S. Pat. No. 4,620,051, the entire disclosure of which is incorporated herein by reference. The process of the present invention can be carried out in fixed, moving, fluidized, ebulating or entrained bed reactors. For experimental purposes and, obviously, to permit accurate measurement and precise control of the process variables, the runs hereinafter set forth in the examples were conducted in a fixed bed reactor.

During operation, in accordance with the present invention, it has been found that small amounts of the feedstock are converted to coke, which is then deposited on the catalyst and contributes to a decline in catalyst activity and selectivity to ethylene. Accordingly, it is desirable to periodically regenerate the catalyst by conventional techniques of carbon removal, such as heating with an oxygen-containing gas, preferably air. During such regeneration, it may also be desirable to use inert gas or steam dilution to control coke burn-off, as is also well known to those skilled in the art.

In accordance with the present invention, the addition of steam to the feed hydrocarbon is preferred because it extends the effective life of the catalyst between regenerations. Preferably, free oxygen is substantially absent during the hydrocarbon conversion process of this invention, so as to minimize the formation of CO and $CO_2$. Furthermore, the catalyst can also be pre-treated, before use in the process of this invention, with inert gases (e.g., $N_2$) or steam or hydrogen gas, while the catalyst composition is being heated to the desired reaction temperature, as has been described in U.S. Pat. No. 4,620,051.

Any suitable reaction conditions for the hydrocarbon conversion process of this invention can be employed. Preferred reaction conditions are those that cause dehydrogenative cracking of the feed hydrocarbon(s) (e.g., of propane to ethylene, and of butanes to propylene and ethylene). The gas hourly space velocity (GHSV) of the feed gas generally is in the range of from about 100 to about 3,000 cc hydrocarbon feed/cc catalyst/hour, and preferably is in the range of from about 500 to about 1,000 cc/cc/hour. The operating pressure generally is in the range of from about 0.1 psia to about 100 psia, and preferably is in the range of from about 1 psia to about 60 psia. If steam is present, the volume ratio of steam to hydrocarbon in the feed generally is in the range of from about 0.1:1 to about 10:1, and more preferably is in the range of from about 0.3:1 to about 5:1. The reaction temperature generally is in the range of from about 550° C. to about 800° C., preferably is in the range of from about 600° C. to about 770° C., and more preferably is in the range of from about 620° C. to about 700° C.

The reaction product of the process of this invention generally contains propylene, ethylene, propane, ethane, methane, free hydrogen and carbon oxides. The components of the reaction product (in particular the desirable $C_2$ and $C_3$ olefins) can be separated and recovered by any of the conventional separation means (such as cryogenic distillation, membrane separation, absorption, and the like). Unconverted $C_3$ and/or $C_4$ feed hydrocarbons can be separated from the components of the reaction product, and can be recycled to the reactor (conversion zone) of the conversion process of this invention.

The solid two compositions of matter of this invention, which are used as catalysts in the hydrocarbon conversion process of this invention, can be prepared by any suitable method. The first composition of matter, a mixture of zinc oxide and at least one manganese oxide (i.e., MnO and/or $Mn_2O_3$ and/or $Mn_3O_4$ and/or $MnO_2$, and the like), can be prepared by mixing zinc oxide and at least one dissolved suitable manganese compound, preferably dissolved in water, drying the obtained mixture, and then calcining the dried mixture (preferably at about 750° C. to about 800° C., in a free oxygen containing gas atmosphere, such as air) so as to substantially convert the manganese compound(s) to manganese oxide. Non-limiting examples of suitable manganese compounds are $Mn(NO_3)_2$, Mn(II) carboxylates such as $Mn(CH_3CO_2)_2$, $Mn(HCO_3)_2$, and $Mn(HSO_4)_2$, hydrates of the above compounds, and mixtures of the above compounds. The composition of matter can be shaped (e.g., by extrusion or pelletizing) and sieved to a desired particle size. Generally, the first composition of matter of this invention contains about 0.1 to about 30 weight-% Mn (expressed as element), preferably about 0.5 to about 10 weight-% Mn.

The second composition of matter of this invention, consisting essentially of zinc oxide, at least one manganese oxide and calcium oxide, can be prepared by mixing zinc oxide, at least one dissolved suitable manganese compound (preferably dissolved in water) and at least one dissolved suitable calcium compound (preferably dissolved in water), drying the obtained mixture, and then calcining the dried mixture (preferably at about 750° C. to about 800° C., in a free oxygen containing atmosphere such as air), so as to substantially convert the manganese compound(s) to manganese oxide and the calcium compound(s) to calcium oxide. Examples of suitable manganese compounds are listed above. Non-limiting examples of suitable calcium compounds are $Ca(NO_3)_2$, calcium carboxylates such as $Ca(CH_3CO_2)_2$, $Ca(HCO_3)_2$, hydrates of the above compounds, and mixtures of the above compounds. The composition of matter can be shaped and sieved, as described above. Generally, the second composition of matter of this invention contains about 0.1 to about 30 weight-% Mn and about 0.1 to about 20 weight-% Ca, preferably about 0.5 to about 10 weight-% Mn and about 0.5 to about 10 weight-% Ca. The weight percentage of oxides of Mn and Ca in the second catalyst composition is less than about 50 weight-% (with the balance of more than about 50 weight-% being zinc oxide).

The following examples are presented to further illustrate this invention and are not to be considered as unduly limiting the scope of this invention.

EXAMPLE I

This example illustrates the preparation of manganese oxide containing catalyst compositions which are effective as butane cracking catalysts.

Catalyst Composition A was a control catalyst composition, in accordance with U.S. Pat. No. 4,621,163, consisting essentially of manganese oxide as minor component and magnesium oxide as support material. Catalyst Composition A contained 4 weight-% Mn. It was prepared by mixing, in an electric blender, 150 grams of $Mg(OH)_2$, 39.1 grams of a 50-weight aqueous solution of $Mn(NO_3)_2$ and enough distilled water to provide a thick paste. The material was dried at 120° C., and then calcined in air at 775° C. for 4 hours. The calcined material was ground and sieved, and a 20–40 mesh fraction was collected.

Catalyst Composition B was a control catalyst composition, substantially in accordance with U.S. Pat. No. 4,159,970, consisting essentially of manganese oxide as minor component and calcium oxide as support material. Catalyst Composition B contained 4 weight-% Mn. It was prepared by impregnation of $Ca(OH)_2$ with a 50 weight-% aqueous solution of $Mn(NO_3)_2$. The obtained material was dried at 120° C. and then calcined in air at 775° C. for 3 hours.

Catalyst Composition C (Invention) consisted essentially of manganese oxide as minor component and zinc oxide as support material. Catalyst Composition C contained 4 weight-% Mn. It was prepared by mixing 100 grams zinc oxide, 26 grams of an aqueous 50 weight-% $Mn(NO_3)_2$ solution and enough water to obtain a thick paste. The material was dried overnight at 115° C. and calcined in air at 775° C.

Catalyst Composition D (Invention) consisted essentially of manganese oxide and calcium oxide as minor components, and zinc oxide as support material. Catalyst Composition D contained 4 weight-% Mn and 3 weight-% Ca. It was prepared substantially in accordance with the procedure for Catalyst Composition C except that $Ca(NO_3)_2.4H_2O$ was used in addition to $Mn(NO_3)_2$.

EXAMPLE II

This example illustrates n-butane cracking tests at various temperatures and in the presence of steam, utilizing the catalyst composition described in Example I.

A gaseous feed mixture of n-butane and steam was introduced into a 15 mm ID quartz tube at a rate of 100 cc n-butane per minute and 100 cc steam per minute. The quartz tube reactor was filled with either 25 cc of Catalyst Composition A or B, or 15 cc of Catalyst Composition C, described in Example I. The temperature of the reactor was gradually increased from about 620° C. to about 720° C. during each test. The gaseous effluent was sampled every 5 minutes and analyzed by means of a Hewlett-Packard 5880 gas chromatograph. Test results are summarized in Table I.

TABLE I

| Catalyst Composition | Temp. (°C.) | % Conversion of n-Butane | % Selectivity[1] to | | | | % Yield[2] of Ethylene and Propylene |
|---|---|---|---|---|---|---|---|
| | | | Ethylene | Propylene | Ethane | Methane | |
| A | 656 | 12 | 34 | 27 | 21 | 10 | 7 |
| (Control) | 684 | 22 | 37 | 27 | 21 | 11 | 14 |
| | 698 | 33 | 38 | 25 | 21 | 11 | 21 |
| | 722 | 47 | 40 | 23 | 20 | 12 | 30 |
| B | 617 | 6 | 26 | 43 | 15 | 0 | 4 |
| (Control) | 641 | 10 | 27 | 41 | 13 | 15 | 7 |
| | 664 | 20 | 28 | 40 | 12 | 16 | 14 |
| | 689 | 31 | 29 | 38 | 11 | 17 | 21 |
| | 715 | 46 | 31 | 37 | 9 | 18 | 31 |
| C | 619 | 15 | 28 | 24 | 29 | 11 | 8 |
| (Invention) | 645 | 30 | 24 | 23 | 27 | 13 | 14 |
| | 670 | 42 | 22 | 21 | 27 | 14 | 18 |
| | 696 | 42 | 34 | 20 | 28 | 10 | 23 |
| | 725 | 40 | 34 | 25 | 20 | 12 | 24 |

[1]Yield of each product ÷ n-butane conversion × 100
[2](Selectivity of ethylene + selectivity of propylene) × n-butane conversion ÷ 100

Test data summarized in Table I indicate that Mn/ZnO (Catalyst Composition C) was more effective than Mn/MgO) (Catalyst Composition A) and Mn/CaO (Catalyst Composition B) for selectively converting n-butane to the desirable olefins (ethylene and propylene), at reaction temperatures of up to about 700° C.

EXAMPLE III

This example illustrates the beneficial effect of the presence of calcium oxide in a manganese oxide/zinc oxide catalyst composition. Test conditions were essentially the same as those described in Example II, except that the reaction temperature was about 750°–770° C. Test results are summarized in Table II.

TABLE II

| Catalyst Composition | Temp. (°C.) | % Conversion of n-Butane | % Selectivity[1] to | | | | |
|---|---|---|---|---|---|---|---|
| | | | Ethylene | Propylene | Ethane | Methane | $H_2$ |
| C | 746 | 50 | 32 | 29 | 16 | 15 | 18 |
| (Mn/ZnO) | 772 | 63 | 34 | 33 | 9 | 18 | 14 |
| | 770 | 68 | 36 | 27 | 13 | 16 | 18 |
| D | 751 | 60 | 37 | 20 | 19 | 16 | 17 |
| (Mn/Ca/ZnO) | 750 | 59 | 37 | 20 | 18 | 16 | 18 |

Test data summarized in Table II indicate that Catalyst Composition D (manganese oxide+calcium oxide+zinc oxide) was more effective than Catalyst Composition C (manganese oxide+zinc oxide) in converting n-butane to ethylene, at a reaction temperature of about 750° C. Based on these test results, it is concluded that this beneficial effect of CaO will also prevail at temperatures at or below about 700° C.

Reasonable variations, modifications, and adaptations for various usages and conditions can be made within the scope of the disclosure and the appended claims, without departing from the scope of this invention.

That which is claimed is:

1. A process for converting hydrocarbons to less saturated hydrocarbons which comprises the step of contacting a feed comprising at least one hydrocarbon selected from the group consisting of propane, n-butane and isobutane with a solid catalyst composition consisting essentially of zinc oxide and manganese oxide, at a temperature of about 620° to about 700° C., under such contacting conditions as to convert at least a portion of said at least one hydrocarbon contained in said feed to at least one less saturated hydrocarbon containing fewer carbon atoms per molecule than said at least one hydrocarbon contained in said feed.

2. A process in accordance with claim 1, wherein said at least one hydrocarbon contained in said feed is n-butane and said at least one less saturated hydrocarbon is selected from the group consisting of ethylene and propylene.

3. A process in accordance with claim 1, wherein said solid catalyst composition contains about 0.1 to about 30 weight-% Mn.

4. A process in accordance with claim 1, wherein said at least one hydrocarbon contained in said feed is n-butane; and said solid catalyst composition consists essentially of (i) zinc oxide as major component, and (ii) manganese oxide as minor component.

5. A process in accordance with claim 1, wherein said contacting conditions comprise a pressure in the range of from about 1 to about 60 psia.

6. A process in accordance with claim 1, wherein said contacting is carried out in the presence of steam.

7. A process in accordance with claim 6, wherein the volume ratio of steam to said at least one hydrocarbon in said feed is in the range of from about 0.1:1 to about 10:1.

8. A process in accordance with claim 1, wherein said catalyst composition contains about 0.5 to about 10 weight-% Mn.

9. A process for converting hydrocarbons to less saturated hydrocarbons which comprises the step of contacting a feed comprising at least one hydrocarbon selected from the group consisting of propane, n-butane and isobutane with a solid catalyst composition consisting essentially of zinc oxide, manganese oxide and calcium oxide, at a temperature of about 620° to about 700° C., under such contacting conditions as to convert at least a portion of said at least one hydrocarbon contained in said feed to at least one less saturated hydrocarbon containing fewer carbon atoms per molecule than said at least one hydrocarbon contained in said feed.

10. A process in accordance with claim 9, wherein said at least one hydrocarbon contained in said feed is n-butane, and said at least one less saturated hydrocarbon is selected from the group consisting of ethylene and propylene.

11. A process in accordance with claim 9, wherein said at least one hydrocarbon contained in said feed is n-butane; and said solid catalyst composition consists essentially of (i) zinc oxide as major component, (ii) manganese oxide as first minor component and (iii) calcium oxide as second minor component.

12. A process in accordance with claim 9, wherein said solid catalyst composition contains about 0.1 to about 30 weight-% Mn and about 0.1 to about 20 weight-% Ca.

13. A process in accordance with claim 12, wherein said solid catalyst composition contains more than about 50 weight-% zinc oxide.

14. A process in accordance with claim 12, wherein said catalyst composition contains about 0.5 to about 10 weight-% Mn, about 0.5 to about 10 weight-% Ca, and more than about 50 weight-% zinc oxide.

15. A process in accordance with claim 9, wherein said contacting conditions comprise a pressure in the range of from about 1 to about 60 psia.

16. A process in accordance with claim 9, wherein said contacting is carried out in the presence of steam.

17. A process in accordance with claim 16, wherein the volume ratio of steam to said at least one hydrocarbon in said feed is in the range of from about 0.1:1 to about 10:1.

* * * * *